United States Patent [19]

Bonomini et al.

[11] 4,269,708
[45] May 26, 1981

[54] HEMODIALYSIS AND/OR ULTRAFILTRATION APPARATUS

[76] Inventors: Vittorio Bonomini, Via Siepelunga 30; Giovanni Ruggeri, Via Boves 4, both of Bologna, Italy

[21] Appl. No.: 35,744

[22] Filed: May 3, 1979

[30] Foreign Application Priority Data

May 3, 1978 [IT] Italy ................ 3415 A/78

[51] Int. Cl.³ ............................................ B01D 31/00
[52] U.S. Cl. ..................... 210/90; 210/103; 210/137; 210/195.2; 210/254; 210/257.2; 210/295; 210/321.3
[58] Field of Search ............... 210/321 B, 22, 90, 103, 210/137, 188, 254, 195.2, 266, 86, 295, 433 M, 257.2, 321 A

[56] References Cited

U.S. PATENT DOCUMENTS

| | | | |
|---|---|---|---|
| 3,529,363 | 9/1970 | Versaci | 210/321 B |
| 3,774,762 | 11/1973 | Lichtenstein | 210/94 |
| 3,814,249 | 6/1974 | Eaton | 210/86 |
| 3,865,726 | 2/1975 | Chibata et al. | 210/152 |
| 3,946,731 | 3/1976 | Lichtenstein | 210/87 |
| 4,021,341 | 5/1977 | Cosentino et al. | 210/87 |
| 4,031,008 | 6/1977 | Anno | 210/137 |
| 4,113,614 | 9/1978 | Rollo et al. | 210/90 |
| 4,123,353 | 10/1978 | Hakansson et al. | 210/22 C |
| 4,127,481 | 11/1978 | Malchesky et al. | 210/22 A |

OTHER PUBLICATIONS

"Unattended Overnight Home Dialysis", J. W. Eschback et al, Am. Soc. Art. Int. Organs, vol. 12, 1966, pp. 346-356.

*Primary Examiner*—Peter A. Hruskoci
*Assistant Examiner*—David R. Sadowski
*Attorney, Agent, or Firm*—Pollock, Vande Sande & Priddy

[57] ABSTRACT

Portable hemodialysis apparatus which can be used for dialysis and/or ultrafiltration, or hemoperfusion. Separate circuits are provided for blood and for the ultrafiltrate and the dialysis solution. The blood circuit includes a pump in which the flexible tube is periodically throttled, causing blood to be drawn from the patient and advanced under pressure through the blood circuit. A similar pump is included in the circuit for the dialysis solution. The output side of the latter pump is selectively connectable either with the inlet of the dialyzer or with an ultrafiltrate collection station, while the input side of the latter pump is selectively connectable with the outlet of the dialyzer either through the dialysis liquid supply tank or directly via a shunt line. A lighter auxiliary tank is also provided for temporary freedom of movement with respect to the normal supply tank.

8 Claims, 5 Drawing Figures

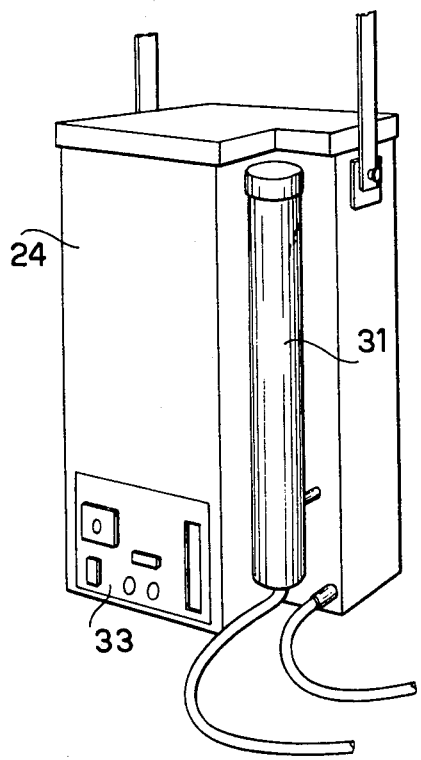
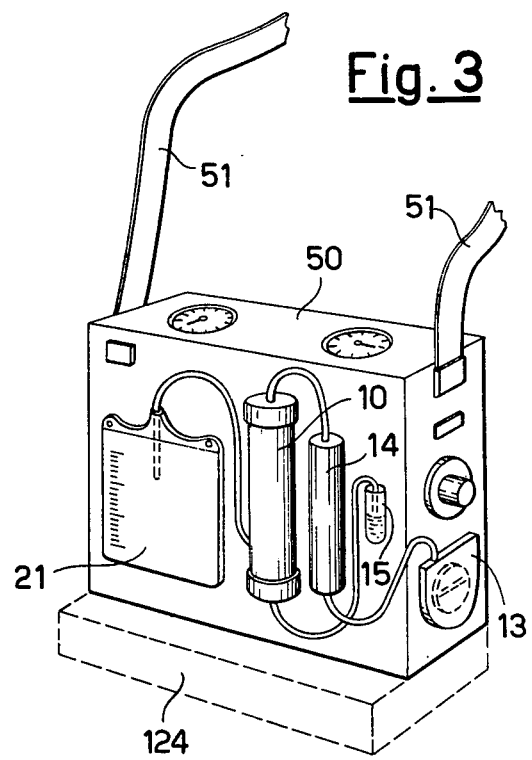
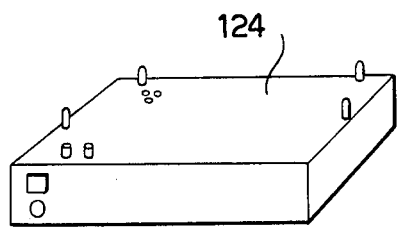

HEMODIALYSIS AND/OR ULTRAFILTRATION APPARATUS

The present invention relates to hemodialysis apparatus for the extracorporeal depuration of blood. More particularly, the invention relates to a portable hemodialysis apparatus, by which the patient is not bound to fixed hemodialysis equipment.

The increasing importance of hemodialysis to assure the depuration of blood from scoriae and toxic substances is well known. It suffices to mention that, whereas the resolutive therapy of chronic renal insufficiency can be, by kidney transplantation, drawn from a donor (either living or dead), the result of such an operation, is uncertain, and the probabilities of keeping the patient alive by periodic hemodialysis treatment are much higher, as confirmed by worldwide statistics.

It is thus clear that hemodialysis is the indispensable treatment, both for patients awaiting kidney transplantation, and for patients for whom, for whatever reason, such an operation is impossible or momentarily impractical.

Hemodialysis is a matter exchange process between two liquid phases, one of which is the blood, whereas the other is a solution having a controlled concentration of certain predetermined components. The exchange takes place through a membrane of a well known type, adapted to permit the passage of molecules of predetermined maximum size and therefore of a predetermined maximum molecular weight.

In the course of the hemodialysis the patient is deprived of a significant predetermined amount of water and of scoriae and toxic substances which pass into the dialysis liquid. In other words the hemodialysis, besides true dialysis, also includes a phase, important as well for purposes of the treatment, of ultrafiltration of the water contained in the blood.

The standard hemodialysis apparatus, normally installed in hospitals for the service of a number of patients, generally comprises an extracorporeal circuit for the blood and a circuit for the dialysis liquid. The blood, drawn by means of a pump from a blood vessel of the patient, passes through the dialyzer, in which countercurrent exchange with the dialysis liquid takes place through a semipermeable membrane, to return to a vein of the patient. At the outlet of the dialyzer, control and safety devices are provided for the purpose of assuring that blood clots and/or air bubbles cannot, by error or accident, reenter with the blood flow into the corporeal circuit (with readily understandable consequences), these devices further assure the compatibility of the reentry pressure with the blood pressure existing in the patient's body.

The circuit for the dialysis liquid comprises a high capacity tank (150 to 300 liters), which is fed with demineralized water and in which a solution is prepared having a predetermined and desired concentration of certain components. Such, a solution, suitably heated to a predetermined temperature consistent with that of the blood in the body circuit (to forestall possible problems of a cardiovascular nature, apart from an uneasy feeling of bodily discomfort, mainly of intense cold, on the part of the patient), passes through the dialyzer in countercurrent flow with respect to the blood, to be thereafter directly discharged as waste.

Hemodialysis treatment (normally having a duration of about four hours and a repetition frequency of three times per week), comprises two phases, namely, (a) true dialysis, in which toxic substances and scoriae (normally small molecules) pass through the semipermeable membrane from the blood to the dialysis liquid, and (b) ultrafiltration, in which a pressure difference between the blood circuit and the circuit for the dialysis liquid, more precisely a reduced pressure in the latter circuit, causes the blood content of water to be reduced by a predetermined amount.

Apart from the clinical problems in hemodialysis treatment, relating to the patient's survival, the following additional problems exist:

(1) The patient is indissolubly bound to a dialysis center, without being able to leave for periods exceeding 48 hours.

(2) Damage to the hemodialysis apparatus of whatever kind or origin poses mortal danger for all patients depending on the apparatus.

(3) Besides being itself very costly and cumbersome, the apparatus requires special auxiliary parts, such as a weighing or balance bed, capable of indicating during the operation the progressive reduction in the weight of the patients due to water elimination by ultrafiltration, which occurs simultaneously with the dialysis.

(4) The costs not only of construction, but even more of operation of hemodialysis apparatus (specialized personnel permanently attending to the operation thereof, enormous water and electric power consumption, etc.) are presently very high and, if account is taken of the constant increase in the number of patients needing this treatment it can be predicted that, in the long run, such costs can become untolerable.

Recent attempts have been made and reported for providing portable hemodialysis apparatus, adapted to permit the patient to enjoy at least limited freedom of allowing the hemodialysis to be carried out at home, the costs being thereby markedly reduced and, most importantly, rendering the patient independent from the hemodialysis hospital center. Among these attempts, a particularly noteworthy one for the comprehension of the present invention is the so-called wearable artificial kidney as described and illustrated in the paper by W. J. Kolff, "Concepts, Critiques and Comments: Wide and Varied (a Festschrift in honor of David Rose)", published November 1976.

This apparatus comprises a hollow fiber dialysis in which the exchange between the patient's blood, as drawn by a single needle system and an anti-regurgitation valve takes place countercurrently with the dialysate. The dialysate is produced by providing a negative pressure in the dialysate compartment which obtains fluid by ultrafiltration, the dialysate volume being designed at about 500 mls. The dialysate is regenerated via a small regeneration system (based on a replaceable absorption unit) on each pass through the dialyzer.

The circulation of both the blood and the dialysate takes place thanks to a special pump, comprising two ventricles which are alternatively compressed by means of an actuator driven by a small 12 volt DC motor. During the diastolic phase, the blood is drawn from the patient's body through the said single needle system, a valve being provided to prevent blood from being drawn from the extracorporeal circuit, and into the ventricle, whereas, during the systolic phase, the blood is ejected from the pumping ventricle and flows through the dialyzer, to return to the patient through the same single needle system. Devices are to be provided for safety, e.g., against air embolisms.

As regards the dialysate side of the system, the dialyzing fluid is supplied by an accumulator, whereas the ultrafiltrate being generated is collected into a particular bag for later disposal.

The wearable module is intermittently connected to a 20 liter tank, receiving the fluid as ejected by the pump and feeding the absorption unit, during this time both the dialysate accumulator and the ultrafiltrate collector are not operative.

As a matter of fact, the patient can be disconnected from the 20 liter tank for no more than 15 minutes, i.e., for approximately two-thirds of the dialysis time the patient must be connected, even through long connection lines, to the 20 liter tank.

According to the data reported in the Kolff paper, the wearable artificial kidney permits the dialysis to be carried out at home or wherever a 12 volt electrical source is available, the dialysis time, both for the true dialysis and for the ultrafiltration, being not less than five hours, since the ultrafiltration occurs at a rate of about 700 mls/hour.

Another problem of above apparatus is that of the flow limitation resulting from the intermittent operation of pump and by the use of the single needle system (the latter in turn being necessary due to the pump type), which can be selected between 0 and 250 mls per minute, whereas flow rates of 300 mls and more per minute are more suitable for optimum hemodialysis.

The main purpose of the present invention is that of providing a portable hemodialysis apparatus in which the blood to be depurated is continuously drawn from the patient's body, and continuously injected again at a different point, whereas the dialysis solution is continuously circulated and regenerated, being rather small in volume.

Another purpose of the present invention is to provide a portable hemodialysis apparatus in which the treatment, besides being able to take place wherever a suitable source of electrical power is available, has a duration no longer than that of the standard hospital operation.

Another purpose of the present invention is to provide a portable apparatus, permitting either dialysis, and/or ultrafiltration, or hemoperfusion to be carried out.

These and other purposes are achieved by means of a portable dialysis apparatus, of the type comprising a first blood circuit and a second circuit for the ultrafiltrate and the dialysis solution, the exchange between the blood and the dialysis liquid taking place through a semipermeable membrane, character the circuit for the blood including a suction and circulation pump or the type in which the flexible tube in which the blood is circulated is periodically throttled by at least one element of the pump head maintained in throttling engagement with the blood tube for at least a length thereof, whereby blood is drawn from the body of the patient and advanced under pressure through the blood circuit, and the circuit for the dialysis liquid includes a pump identical to that for the blood circuit, the latter pump having its suction side in communication with either the outlet of the dialyzer or with a supply of dialysis liquid under the control of suitable valve means, the output side of the pump being in communication either with the inlet of the dialyzer or with a collection bag, under the control of further valve means, a pressure metering device being inserted, upstream of the pump.

According to the preferred embodiment of the invention, the circuit for the dialysis liquid comprises (a) a first configuration in which the suction side of the pump is directly connected to the outlet side of the dialyzer, whereby a reduced pressure, on the dialysis liquid side, can be established in the dialyzer, thus permitting the water contained in the blood to be extracted by ultrafiltration, this water being discharged by the pump into a graduated collecting bag, which permits the amount or weight of extracted water to be readily estimated, and (b) a second configuration, in which the suction side of the pump is directly connected to the outlet of a tank containing a water solution having a predetermined content of selected components, thus forming the dialysis liquid, the tank being provided with means for the control and adjustment of the temperature of the dialysis liquid, and the outlet of the pump being in direct communication with the inlet of the dialyzer, an absorption filter being provided between the outlet of the dialyzer and the inlet of the tank, to permit the dialysis liquid, after the matter exchange in the dialyzer, to be regenerated by absorption of the toxic substances.

According to another feature of the present invention, the treatment of the blood comprises a first step in which the said first configuration is operative and only ultrafiltration takes place until a predetermined amount of water is removed from the blood of the patient, the second step being the true dialysis, in which the dialysis circuit is in its said second configuration.

According to a further feature of the present invention, an auxiliary tank is provided, adapted to be substituted for the said supply tank, and containing a much smaller amount of dialysis liquid than the latter, to permit the patient to be freed from the main supply tank for a limited time.

The several features and advantages of the present invention will become apparent from the following detailed description of a preferred embodiment, with reference to the enclosed drawings in which:

FIG. 2 is a perspective view of the tank for the dialysis solution;

FIG. 3 is a perspective view of the portable unit to be worn by the patient undergoing the dialysis;

FIG. 4 is a perspective view of an auxiliary device for the unit of FIG. 3 and

Figure 1:
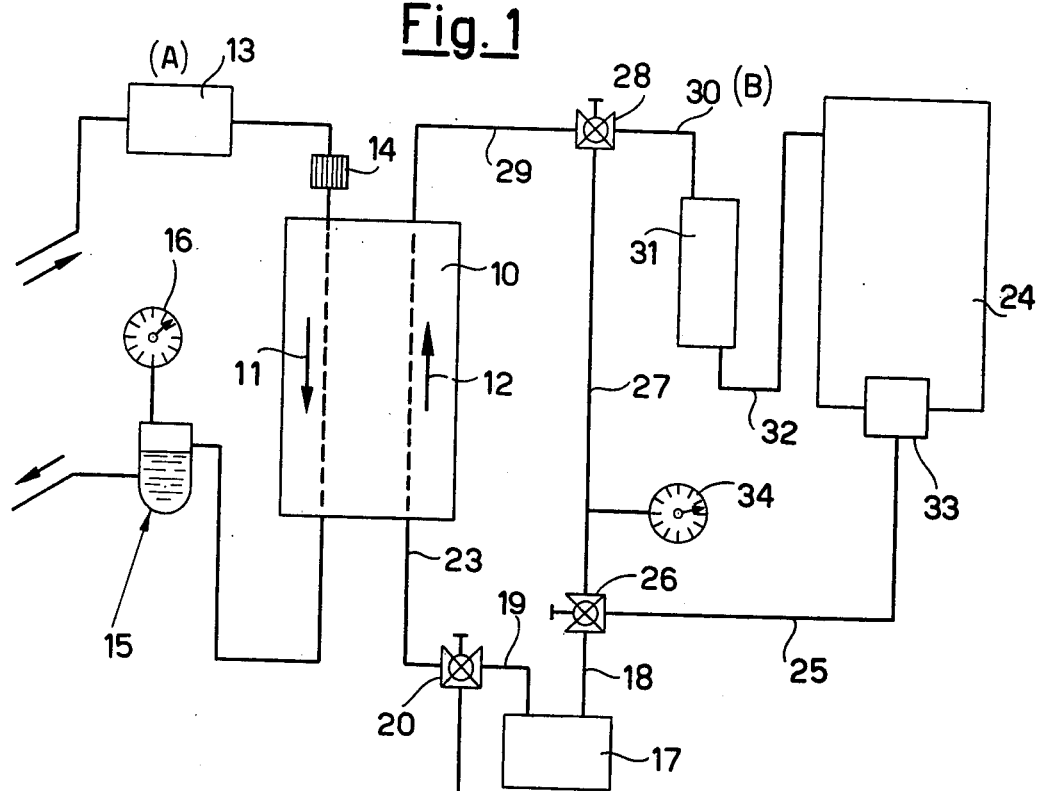
FIG. 1 is a schematic view of the apparatus of the present invention.

Referring first to FIG. 1, there are shown two circuits, namely, one for the blood (A) and one for the dialysis liquid and for the ultrafiltrate (B).

Reference 10 indicates the dialyzer, which can be of a well-known type, e.g., of the type in which the blood runs along a cavity formed between two semipermeable membranes, whereas the dialysis liquid flows countercurrently on the outer surfaces of both membranes.

According to another preferred embodiment, the dialyzer comprises a bundle of capillary fibers, the inside passage of which is run by the blood, whereas the dialysis liquid flows countercurrently along the outer surfaces of the fibers. Of course, any other type of dialyzer known in the art and of suitable size, can be used, provided that it permits the desired exchange between the blood and the dialysis liquid. The blood is circulated in dialyzer 10 in the direction indicated by arrow 11, whereas the dialysis liquid circulates in the direction indicated by arrow 12. Turning now more particularly to circuit A, it comprises a pump 13, to be described in more detail described, a filter 14, containing a material suitable for hemoperfusion, e.g., special activated carbon, and having the purpose of removing toxic substances from the blood before it enters the dialyzer, thus increasing the efficacy of the depuration. Filter 14 is not compulsory and is of the replaceable type. Before the blood reenters the body circuit of the patient, it is passed through a device 15, of a type known per se, for the purpose of preventing blood clots and air bubbles from being entrapped with the blood flow. In addition, a pressure meter 16 permits the pressure of the blood being fed back to the patient's vein to be adjusted to a suitable value.

The blood is drawn either from a vein or from an artery, whereas the return of the blood to the patient's body always takes place through a vein.

Part (B) of the apparatus, i.e., the circuit for the dialysis liquid, comprises a pump 17, of the same type as pump 13, having a suction tube 18 and a delivery tube 19. The latter, through a suitable two-way valve 20, can be placed in communication either with a collection bag 21 (via connecting line 22), having metering lines permitting measurement of the amount of liquid contained therein, or with the inlet side of dialyzer 10, via connecting line 23. Tube 18 is connected, by means of valve 26, either to the supply tank 24, through a line 25, or to a shunt line 27, which in turn, through two-way valve 28, can be directly connected to the outlet of dialyzer 10 (via connecting line 29).

Valve 28 is connected via line 30 to a replaceable filter cartridge 31, positioned upstream of tank 24, and having the purpose of regenerating the dialysis liquid by absorbing the toxic substances extracted from the blood in the dialyzer.

The outlet of cartridge 31 is connected via line 32 to tank 24, and a device 33 is provided for the purpose of controlling the temperature of the dialysis liquid being drawn by pump 17 to a predetermined value. Cartridge 31 too is charged with an absorption material, such as activated carbon, serving for the stated purpose and well known in art. In the shunt line 27 a pressure gauge 34 is inserted, in order to measure the reduced pressure or vacuum generated by pump 17 in the dialyzer 10 during the ultrafiltration phase.

Figure 5:
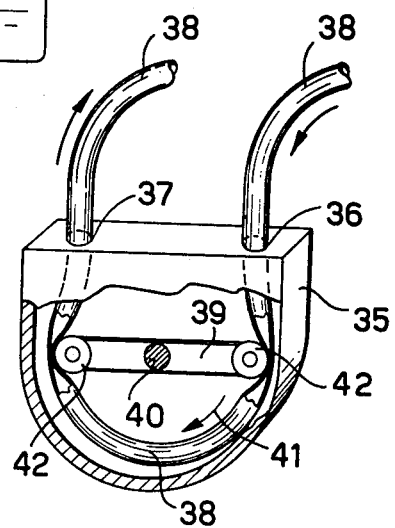
FIG. 5 is a perspective view of a pump used for the circulation of the blood as well as of the dialysis liquid.

FIG. 5 shows the head or operative part of pumps 13 and 17. More particularly, this head comprises a casing 35, in the upper part of which two apertures 36 and 37 are formed for the entry and a exit of the tube 38. The lower part has a curved shape, to which tube 38 is thoroughly adhered. The actuator 39 of the pump head is mounted on the outlet shaft 40 of an electric motor (not shown), the actuator being rotated in the direction of arrow 41. Both ends of the actuator 39 are provided with idler rollers 42, the distance of the rollers from the axis of the shaft 40 being selected so that tube 38, which is of suitable collapsible material (e.g., plastic material), is throttled between the roller and the adjacent inner surface of casing 35. The rotation of the actuator 39 in direction of the arrow 41 causes pumping effect to occur.

Turning now to FIGS. 2 and 3, a preferred embodiment of the portable hemodialysis apparatus is shown, comprising a casing 50, which can be attached to the patient's chest by means of straps or braces 51. The casing 50 comprises all the previously described components, apart from the tank 24, the temperature control and adjusting device 33 and the filter cartridge 31, which are formed as a unit and shown in FIG. 2.

The two pumps 13 and 17 are mounted at the two opposite sides of casing 50 and their motors are driven by any suitable electric source to which the motors are adapted.

Instead of the valves 20, 26 and 28, quick connecting and disconnecting joints could be provided, according to the two phases of the operation of the apparatus.

The auxiliary unit 124 (shown in FIG. 4 and adapted to be positioned as shown in dashed lines in FIG. 3), permits tank 24 to be temporarily detached, to permit the patient, wearing only the portable unit, to be completely free from the weight of supply tank 24 with its normal capacity of about 20 liters.

The collecting bag 21 is normally removed after the ultrafiltration phase, and possibly replaced by a filter cartridge identical to filter 31, the latter being in this case omitted from the unit shown in FIG. 2.

The latter is normally independently mounted, possibly on caster wheels, and can be quickly connected to the unit of FIG. 3, to give to the configuration of FIG. 1.

Turning now to the operation of the portable apparatus of the present invention, as already mentioned two phases can be identificated, namely ultrafiltration and dialysis.

(1) Ultrafiltration

In this phase, blood is drawn the pump 13, whereas a reduced pressure is established in the dialyzer, on the dialysis liquid side, by means of pump 17, connected by, shunt line 27 and line 29, to the outlet of dialyzer 10, while the output side of pump 17 is connected, via lines 19 and 22, to collection bag 21.

Of course, valves 20, 26 and 28 must be suitably controlled to provide the above described circuit.

(2) Dialysis

After ultrafiltration is completed, valve 20 is switched to connect the output side of pump 17, via lines 19 and 23, to the inlet of the dialyzer, while valves 26 and 28 are switched to exclude shunt line 27, the circuit of the dialysis liquid then comprising filter cartridge 31, tank 24 and temperature control device 33. Dialysis then takes place for a predetermined time, at the end of which the portable unit is disconnected from the patient's blood vessels, and is ready for the next operation.

The apparatus of the present invention has been tested in vivo on volunteer patients, both those awaiting kidney transplantation those undergoing conventional hemodialysis to depurate their blood.

Apart from the clinical results to be summarized hereinbelow, the patients have constantly indicated a state of well-being apparently superior to that achieved with the standard hemodialysis apparatus.

As regards therapeutical results, it is to be pointed out that one of the very important features of the present apparatus is that of permitting the ultrafiltration to be carried out as a first phase, thus permitting the water to be removed from the patient to be drawn from the very outset, without any significant cardio-circulatory modifications of status of the organism.

Furthermore such a first ultrafiltration permits part of the toxic substances to be removed together with the water, thus simplifying the subsequent dialysis.

The practical tests resulted in a treatment time no longer than that of the fixed standard apparatus or even shorter, due to the ultrafiltration carried out as the first step. The dialysis treatment as carried out with the apparatus of the present invention (I) has been compared with the standard apparatus (III) and with the wearable artificial kidney (II) (as average values calculated from the data reported in the paper by Kolff):

TABLE 1

| Material removed during the first hour of ultrafiltration | | | |
|---|---|---|---|
| | I | II | III |
| H$_2$O mls. | 2500 | 700 | 2500 |
| urea mg | 300 | 112 | 300 |
| uric acid mg | 95 | 37 | 98 |
| creatinine | 18 | 7.5 | 19 |

TABLE 2

| Material removed during the first hour of dialysis | | | |
|---|---|---|---|
| | I | II | III |
| Urea mg | 1500 | 1200 | 1700 |
| uric acid | 550 | 450 | 550 |
| creatinine mg | 1000 | 850 | 1050 |

The above results confirm that the portable apparatus of the present invention permits the hemodialysis to be carried out with performance rates at least comparable with those of the standard hospital treatment, but with the outstanding advantages previously described.

In this connection, it should be noted that the apparatus of the present invention, due to the complete separation between the ultrafiltration and the dialysis phases, permits not only standard hemodialysis to be performed, but also ultrafiltration alone and dialysis alone, by merely suitably adjusting the circuit for the dialysis liquid. Moreover, other similar treatments, such as the hemoperfusion can also be carried out.

The favorable results achieved by the present invention are mainly due to the use of the particular pumps, both on the blood side and on the dialysis liquid side, since no danger exists of damage to the pump during ultrafiltration, when reduced pressure is to be established in the dialyzer and no liquid at least initially passes through the pump 17.

We claim:

1. In a portable dialysis apparatus, of the type comprising a first circuit for blood and a second circuit for ultrafiltration and dialysis liquid, the exchange between the blood and the dialysis liquid taking place through a semipermeable membrane, the improvement comprising
    (a) a pump means in each of said first and second circuits, each said pump means having a head and being of the type in which a flexible tube is intermittently throttled by at least one element of said pump head, said pump head being maintained in throttling engagement with said tube for at least a length thereof;
    (b) means for selectively connecting the output side of the pump means for said dialysis liquid either with the inlet of said dialyzer or with an ultrafiltrate collection station;
    (c) means for selectively connecting the input side of pump means for said dialysis liquid with the outlet of the dialyzer either through a supply tank of dialysis liquid or directly via a shunt line;
    (d) whereby ultrafiltration and dialysis are performable as first and second steps in sequence;
    (e) a pressure meter being arranged in said shunt line upstream of the pump means for said dialysis liquid; and
    (f) said supply tank for said dialysis liquid being provided with temperature control and adjustment means, and a filter for the absorption of toxic substances from the dialysis liquid being mounted between said outlet of said dialyzer and said supply tank.

2. The apparatus according to claim 1, wherein the connection of said output side of said pump means for said dialysis liquid to either the inlet of said dialyzer or to said collection station is selectively established by a switchable two-way valve.

3. The apparatus according to claim 1, wherein the connection of said input side of said pump means for said dialysis liquid to the outlet of said dialyzer through said shunt line is controlled by two-way valves, the switching of which permits said input side to communicate with said outlet either through said shunt line or through said supply tank.

4. The apparatus according to claim 1, wherein each said pump head comprises a casing having a curved portion against which the inner surface of said flexible tube abuts, each said pump means comprising an actuator, drive means for rotating said actuator, said actuator having at least one roller means engaging said tube for a predetermined length and throttling it against the inner surface of said curved portion of said casing.

5. The apparatus according to claim 4, wherein each said actuator comprises two arms, said roller means being attached to the end of at least one of said arms.

6. The apparatus according to claim 1, comprising a filter for the absorption of toxic substances arranged upstream of said dialyzer in said first circuit and a control and safety device arranged downstream of said dialyzer in said first circuit to prevent the entry of blood clots and air into the patient's body, and to control the blood pressure.

7. The apparatus according to claim 1, wherein said supply tank and said filter in said dialysis liquid form a separate unit, the remaining part of the apparatus being mounted to a unitary casiing for attachment to the patient's body.

8. The apparatus according to claim 7, wherein said supply tank is an auxiliary tank of small capacity for temporary attachment to said casing.

* * * * *